United States Patent [19]

Rzeszotarski et al.

[11] Patent Number: 5,032,593
[45] Date of Patent: Jul. 16, 1991

[54] METHOD OF TREATING BRONCHOCONSTRICTION WITH 1,3-UNSYMMETRICAL STRAIGHT CHAIN ALKYL-SUBSTITUTED 8-PHENYLXANTHINES

[75] Inventors: Waclaw J. Rzeszotarski, Millersville; Ronald H. Erickson, Baltimore, both of Md.

[73] Assignee: Marion Merrell Dow Inc., Kansas City, Mo.

[21] Appl. No.: 214,550

[22] Filed: Jul. 1, 1988

[51] Int. Cl.$^5$ .................... A61K 31/52; C07D 473/06
[52] U.S. Cl. .................... 514/263; 544/267; 544/273
[58] Field of Search .................... 544/267; 514/263, 273

[56] References Cited

U.S. PATENT DOCUMENTS

| 4,089,959 | 5/1978 | Diamond | 514/263 |
| 4,593,095 | 6/1986 | Snyder et al. | 544/272 |
| 4,612,315 | 9/1986 | Jacobson et al. | 544/273 X |
| 4,783,530 | 11/1988 | Rzeszotarski et al. | 544/267 |

FOREIGN PATENT DOCUMENTS 1091570 10/1960 Fed. Rep. of Germany .
1140581 12/1962 Fed. Rep. of Germany ...... 544/273

OTHER PUBLICATIONS

Chasin et al., "Advances in Cyclic Nuceotide Research," vol. 7, ed. Greengard et al., Raven Press, N.Y. (1976), pp. 225–264.

Wells et al., J. Med. Chem., vol. 24, No. 8, pp. 954–958 (08/81).
Fredholm et al., European J. Pharmacology, vol. 81, pp. 673–676 (1982).
Persson, Agents Actions, vol. 13, (suppl.), pp. 115–129 (1983).
Bruns et al., Proc. Natl. Acad. Sci. U.S.A., vol. 80, pp. 2077–2080 (04/83).
Rall, "The Pharmacological Basis of Therapeutics", 7th ed., Gilman, et al., ed., MacMillan Publishers, N.Y. (1985), Chap. 25, pp. 589–603.
Hamilton et al., J. Med. Chem., vol. 28, No. 8, pp. 1071–1079 (08/85).
Persson et al., Life Sciences, vol. 38, No. 12, pp. 1057–1072 (1986).
Daly et al., J. Med. Chem., vol. 29, No. 7, pp. 1305–1308 (7/86).
Bruns et al., Molecular Pharmacology, vol. 29, pp. 331–346 (1986).
Daly et al., J. Med. Chem., vol. 28, pp. 487–492 (1985).
Hamilton et al., J. Med. Chem., vol. 30, No. 1, pp. 91–96 (01/87).

*Primary Examiner*—Diana Rivers
*Attorney, Agent, or Firm*—Theresa M. Gillis

[57] ABSTRACT 1,3-Alkyl substituted-8-phenylxanthines in which the straight chain alkyl substituents are different and pharmaceutically acceptable salts of such compounds are disclosed. Preferred compounds have 1-n-propyl-3-methyl and 1-methyl-3-n-propyl substituents. The compounds are potent bronchodilators.

4 Claims, No Drawings

METHOD OF TREATING BRONCHOCONSTRICTION WITH 1,3-UNSYMMETRICAL STRAIGHT CHAIN ALKYL-SUBSTITUTED 8-PHENYLXANTHINES

BACKGROUND OF THE INVENTION a) Field of the Invention

This invention relates to unsymmetrical straight chain alkyl-substituted phenylxanthines which demonstrate potent bronchodilating activity. The compounds are 8-phenylxanthines having a methyl or propyl group at the 1- and 3- positions with the proviso that the 1- and 3-substituents may not be the same and the pharmaceutically acceptable salts of such compounds.

b) State of the Art

Xanthines of various types have been used or proposed as drugs for various indications. For example, theophylline and aminophylline relax the smooth muscle of the bronchial airways and pulmonary blood vessels, thereby acting as pulmonary vasodilators, bronchodilators and smooth muscle relaxants. Like other xanthines these compounds possess the following actions as well: coronary vasodilator, diuretic, cardiac and cerebral stimulant and skeletal muscle stimulant. Dyphylline is another xanthine having activity similar to that of theophylline and aminophylline. Most of these xanthines bear identical alkyl substituents in positions 1 and 3. Nevertheless, a large number of xanthines having different substituents in these positions are known [see, e.g., R.F. Bruns, G.H. Lu, and T. Pugsley, Mol. Pharmacol., 29, 331 (1986); J.W. Daly, W.L. Padgett, and M.T. Shamin, J. Med. Chem , 29, 1305 (1986); J.N. Wells, J.E. Garst, and G.L. Kramer, J. Med. Chem., 24, 954 (1981)] and several have notable pharmacological activity. For example, enprofylline (3-propylxanthine) has bronchodilating and antiasthmatic characteristics [see, e.g., C.G.A. Persson, K.-E.-Andersson and G. Kjellin, Life Sci., 38, 1057 (1986)]and IBMX (3-isobutyl-1-methylxanthine) and related compounds are potent inhibitors of phosphodiesterase [M. Chasin and D.N. Harris, Adv. Cyclic Nucleotide Res., 7, 225 (1976)].

Nevertheless, relatively little prior art exists for 8-phenylxanthines with an unsymmetrical alkyl substitution of the 1 and 3 positions. Bruns et al. [Proc. Natl. Acad. Sci. USA, 80, 2077 (1983)]disclose many 8-arylxanthines. One preferred compound is 1,3-dipropyl-8-(2-amino-4-chlorophenyl)xanthine (PACPX). The only unsymmetrical alkyl-substituted xanthines which Bruns et al. disclose lack an 8-phenyl substituent.

Many 8-arylxanthines are disclosed in U.S. Pat. No. 4,593,095 to Snyder et al., including the preferred compound PACPX. As with Bruns et al., most of the Snyder et al. compounds are symmetrically substituted. Although one of the preferred compounds of the present invention is generically within Snyder's formula, none is exemplified nor claimed. Indeed, the only exemplified unsymmetrically substituted 1,3-dialkyl-8-phenylxanthine is 1-allyl-3-methyl-8-phenylxanthine [U.S. Pat. No. 4,593,095, column 11; see, also, H.W. Hamilton et al., J. Med. Chem., 28, 1071 (1985)].

Other unsymmetrically substituted 1,3-dialkyl-8-phenylxanthines described in the literature are 1-isoamyl-3-isobutyl-8-phenylxanthine [J.W. Daly et al., J. Med. Chem., 28, 487 (1985)], 3-ethyl-1-methyl-8-phenylxanthine [H.W. Hamilton et al., J. Med. Chem., 30, 91-96 (1987)], and 1-hexyl-3-methyl-8-phenylxanthine [H.G.V. Schub, German Patent 1,091,570 (1960)]. The first two compounds have been studied only in binding assays for affinity for the $A_1$ and $A_2$ subtypes of adenosine receptors. For the third compound "drug use" is claimed. The possibility that the therapeutic responses to adenosine receptor antagonists, such as theophylline, may involve such antagonism is uncertain. This uncertainty is based largely on the observation that enprofylline, which is about five-fold more potent than theophylline in man and other species [C.G.A. Perrson, Agents Actions, 13 (Suppl.), 115–129 (1983)], is much less effective than theophylline in diminishing responses to adenosine in all tissues studied, except for the rat hippocampus [B.B. Fridholm and C.G.A. Persson, Eur. J. Pharmacol., 81 673–676 (1982)]. Thus, it is not certain to what extent the two xanthines share common cellular actions or whether adenosine receptor blockade is of significance in the bronchodilator effect that theophylline produces in asthmatic patients [T.W. Rall in "Goodman and Gilman's, The Pharmacological Basis of Therapeutics," 7th Ed., A.G. Gilman, L.S. Goodman, T.W. Rall and F. Murad, eds., MacMillan Publishers, New York 1985, pp. 589–603]. Thus, the potent bronchodilating activity of the compounds of this invention is unexpected and the mechanism by which they produce this pharmacological response remains to be elucidated.

Co-pending application Serial No. 108,990 filed Oct. 1, 1987 (now U.S. Pat. No. 4,783,530) describes various 1,3-alkyl substituted-8-(3,4-or 4-substituted phenyl)xanthines. The 1,3-substituents need not be the same. Among the preferred compounds are: 1-propyl-3-methyl-8-(3-N,N-dimethylaminomethyl-4-hydroxyphenyl)-xanthine and 1-propyl-methyl-8-(4-cyanophenyl-)xanthine.

This invention provides a series of novel 1,3-unsymmetrical straight chain alkyl-substituted 8-phenylxanthines which produce potent bronchodilating activity in a test for reversal of histamine-induced bronchoconstriction, the preferred test for measuring this activity (T.W. Rall, loc. cit.), as well as in a test for prevention of antigen-induced bronchoconstriction in guinea pigs. The compounds also have a decreased tendency to produce unwanted side effects, such as increasing heart rate, decreasing blood pressure and causing emesis, as is seen with prototypic xanthine-type bronchodilators, e.g., theophylline. Binding studies demonstrate that this beneficial bronchodilating action is not correlated with $A_1$- or $A_2$-adenosine receptor binding.

SUMMARY OF THE INVENTION

This invention relates to novel 8-phenylxanthines which are potent bronchodilators. Specifically, this invention provides compounds of the formula:

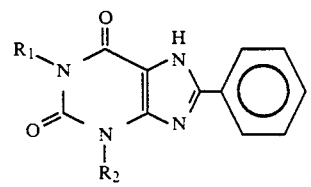

wherein $R_1$ and $R_2$ are saturated straight chain alkyls of one to eight carbons, with the proviso that $R_1$ and $R_2$ are not the same. Compounds of formula I wherein $R_1$ and $R_2$ are straight chain alkyls of one to five carbons, with the proviso that either $R_1$ and $R_2$ must be an alkyl group of at least three carbons, are included. The preferred compounds are 1-methyl-3-n-propyl-8-phenylxanthine and 3-methyl-1-n-propyl-8-phenylxanthine.

The invention includes the pharmaceutically acceptable salts of compounds of the foregoing formula. The invention also relates to the use of these compounds as bronchodilating agents.

DETAILED DESCRIPTION OF THE INVENTION

The compounds of the invention are those having the formula:

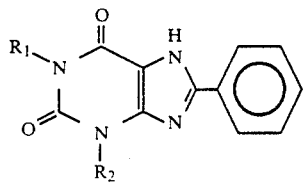

wherein $R_1$ and $R_2$ are straight chain saturated alkyls of one to eight carbons, preferably methyl or propyl, with the proviso that $R_1$ and $R_2$ may not be the same, and pharmaceutically acceptable salts of such compounds. Compounds of formula I wherein $R_1$ and $R_2$ are straight chain alkyls of one to five carbons, with the proviso that either $R_1$ and $R_2$ must be an alkyl group of at least three carbons, are especially provided.

Preferred compounds are those in which $R_1$ is n-propyl and $R_2$ is methyl or $R_1$ is methyl and $R_2$ is n-propyl. The preferred compounds are 1-methyl-3-n-propyl-8-phenylxanthine and 3-methyl-1-n-propyl-8-phenylxanthine.

The compounds of this invention may be used in the form of pharmaceutically acceptable salts or complexes with various inorganic or organic bases. Typical salts include the alkali metal or alkaline earth metal salts, although it is to be appreciated that other nontoxic salts are also intended. The compounds of this invention, by virtue of the acidic proton in the 7 position, can form anions at alkaline pH and, thus, can be advantageously administered as sodium, potassium or ammonium salts, choline salts and complexes with ethylenediamine, for example.

The compounds of the invention are potent bronchodilators, relative to known 8-arylxanthines, as demonstrated by their ability to reverse histamine-induced bronchoconstriction in guinea pigs.

The compounds of the invention may be administered orally or parenterally in conventional dosage unit forms such as tablets, capsules, injectables or the like, by incorporating the appropriate dose of a compound of the indicated formula with carriers according to accepted pharmaceutical practices. Preferably a compound or basic addition salt or complex thereof is administered orally to an animal in a tablet or capsule comprising an amount sufficient to produce bronchodilator activity. Each dosage unit will contain the active medicament in an amount of about 10 mg to about 100 mg. Advantageously, equal doses are administered 4 to 6 times daily to the animal, with the daily dosage regimen being about 40 mg to about 200 mg.

The pharmaceutical carrier employed may be, for example, either a solid or liquid. Exemplary solid carriers include lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent can include any time delay material well known in the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier can vary widely, but preferably will be 25 mg to about 1 g. If a liquid carrier is used, the preparation will be in the form of a syrup, emulsion, soft gelatin capsule, sterile injectable liquid such as an ampule, or an aqueous or nonaqueous liquid suspension.

Of particular applicability is an aerosol dispensing system wherein the active medicament is incorporated with Freon ® (fluorohydrocarbon) or other inert propellant in an aerosol container. Such an aerosol system will deliver a metered dose of about 50 mcg to about 1600 mcg administered as needed.

The compounds may be synthesized according to known methods, for example, as follows: 6-Amino-1-methyl-3-propyluracil and 6-amino-3-methyl-1-propyluracil are prepared by known procedures. [V. Papesch and E.F. Schroeder, J. Org. Chem., 17, 1879 (1952)]. Nitrosation of the respective aminouracils followed by catalytic hydrogenation of the resulting 5-nitroso derivatives affords the corresponding 5,6-diaminouracils, which upon condensation with benzaldehyde give 5-amino-1-methyl-3-propyl-6-phenyliminouracil or 5-amino-3-methyl-1-propyl-6-phenyliminouracil. Ring closure of the respective intermediate to produce 3-methyl-1-propyl-8-phenylxanthine and 1-methyl-3-propyl-8-phenylxanthine is effected with an appropriate dehydrogenating agent, for example, diethyl azodicarboxylate (DEAD) or thionyl chloride.

The foregoing is a general description of how to prepare the compounds of this invention. The following examples illustrate the preparation of specific compounds. This should not be construed as a limitation of the invention as appropriate variations in the starting materials will produce other compounds set forth hereinabove.

EXAMPLE 1

6-Amino-1-methyl-5-nitroso-3-n-propyluracil

6-Amino-1-methyl-3-n-propyluracil (13.2 g, 7.3 mmol) was dissolved in 10–15 ml of acetic acid and the solution was warmed on a hot plate to 60–70° C. Then, with stirring, a solution of sodium nitrite (5.3 g, 7.7 mmol) in 100 ml of water was added in 10 ml portions over 10 minutes. A brownish-purple precipitate formed. The reaction mixture was cooled to 10° C. and the precipitate was collected by vacuum filtration, washed with 10 ml of acetone, and air-dried to give 8.3 g (55%) of 6-amino-1-methyl-5-nitroso-3-propyluracil as a purple solid. $^1$H NMR (DMSO-$d_6$+$D_2O$) δ 0.90 (t, J=7 Hz, 3 H), 1.62 (sextet, J=7 Hz, 2 H), 3.26 (s, 3 H), 3.87 (t J=7 Hz, 2 H).

5,6-Diamino-1methyl-3-n-propyluracil

The 6-amino-1-methyl-5-nitroso-3-n-propyluracil (8.3 g, 40 mmol was slurried with 75 ml of absolute ethanol and 100 mg of 10% Pd/C. The mixture was placed in a Parr bomb that was then pressurized to 80 psi with hydrogen. The bomb was repressurized as needed. After 2 hours, no further uptake of hydrogen was observed. The reaction mixture was filtered to give ca. 1.6 g of starting material. The solvent was removed from the greenish mother liquors by rotary evaporation to give a greenish-yellow solid. Trituration of the solid with ca. 25 ml of methanol gave an off-white solid which was collected by vacuum filtration, washed with methanol (3×5 ml) and ether (3×10 ml), and air-dried to give 4.4 g (70% based on recovered starting material) of 5,6-diamino-1-methyl-3-n-propyluracil which was used directly in the next step.

3-Methyl-1-n-propyl-8-phenylxanthine

A mixture of benzaldehyde (2.5 ml, 25 mmol), the 5,6-diamino-1-methyl-3-n-propyluracil (4.4 g, 22 mmol) from the above step, and 1 ml of acetic acid was refluxed overnight in 60 ml of ethanol. Upon cooling to room temperature, a yellow precipitate formed which was collected by vacuum filtration and washed with ethanol (2×5 ml) and ether (2×5 ml) to give the imine as a pale yellow solid (5.4 g, 84%) which was used directly in the next step. $^1$H NMR (DMSO-d$_6$) δ0.79 (t, J=7 Hz, 3 H), 1.50 (sextet, J=7 Hz, 2 H), 3.34 (s, 3 H), 3.74 (t, J=7 Hz, 2 H), 7.35 (m, 3 H), 7.75 (m, 2 H), 9.57 (s, 1 H).

The imine was then heated in 60 ml of glyme. As the mixture began to reflux, the imine dissolved and diethyl azodicarboxylate (DEAD) (4.4 ml, 4.9 g, 28 mmol) was added through the condenser. Within 5 minutes the solution was filled with a white solid. The solution was cooled and the solid was filtered and washed with ethanol (2×5 ml) and ether (2×5 ml) to give a white solid (4.3 g), The solid was boiled with 750 ml of methanol and filtered hot (2.3 g did not dissolve). Cooling the solution gave a precipitate which was filtered and washed with methanol (3×5 ml) and ether (3×5 ml) to give 1.4 g of the substituted xanthine as a white solid with the consistency of cotton, mp 277–279° C. $^1$H NMR (DMSO-d$_6$) δ 0.89 (t, J=7 Hz, 3 H), 160 (sextet, J=7 Hz, 2 H), 3.51 (s, 3 H), 3.88 (t, J=7 Hz, 2 H), 7.50 (m, 3 H), 8.12 (m, 2 H). IR (KBr) 3175, 1702, 1650 cm$^{-1}$. Anal. Calcd. for C$_{15}$H$_{16}$N$_4$O$_2$: C. 63.37; H, 5.67; N, 19.71. Found: C, 63.34; H, 5.68; N, 19.70. TLC: silica gel; ether:hexane, 55:45; blue fluorescense by UV; Rf=0.39. HPLC: Hamilton PRO-1 column; 30% acetonitrile/70% water buffered with heptanesulfonic acid (pH 3.5) going to 95% acetonitrile over 20 minutes; tR=15.6; K'=6.2.

EXAMPLE 2

6-Amino-3-methyl-5-nitroso-1-n-propyluracil

6-Amino-3-methyl-1-n-propyluracil (10.46 g, 57.8 mmol) was dissolved in 10 ml of acetic acid at 90° C. Then, with stirring, a solution of sodium nitrite (4.19 g, 60.8 mmol) in 100 ml of water was added in 10 ml portions over 5 minutes. A purple color formed immediately followed by a purple precipitate. The mixture was cooled in the freezer for 20 minutes and then the precipitate was collected by vacuum filtration, washed with water (2×30 ml) and acetone (2×10 ml), and air-dried to give 6-amino-3-methyl-5-nitroso-1-n-propyluracil as purple needles (10.02 g, 83%). $^1$H NMR (DMSO-d$_6$+D$_2$O) δ0.89 (t, J=8 Hz, 3 H), 1.55 (sextet, J=8 Hz, 2 H), 3.27 (s, 3 H), 3.80 (t, J=8 Hz, 2 H).

5,6-Diamino-3-methyl-1-n-propyluracil.

6-Amino-3-methyl-5-nitroso-1-n-propyluracil (11.53 g, 54.9 mmol) was slurried with 75 ml of anhydrous ethanol and 200 mg of 20% Pd/C in a Parr bomb. The bomb was pressurized to 80 psi with hydrogen and repressurized as needed during the reaction. After 2.5 hours, no further uptake of hydrogen was observed. The reaction solution was filtered through celite. The solvent was removed by rotary evaporation to give a yellowish solid which was triturated with ethanol: ether (1:1; 100 ml) to give an off-white solid that was collected by vacuum filtration, washed with ethanol: ether (1:1; 2×10 ml) and ether (2×25 ml), and air-dried to give 5,6-diamino-3-methyl-2-n-propyluracil (6.17, 57%) that was used directly in the next step.

1-Methyl-3-n-propyl-8-phenylxanthine

A mixture of benzaldehyde (3.5 ml, 34 mmol), the 5,6-diamino-3-methyl-1-n-propyluracil (6.2 g, 32 mmol) from the above step, and 1 ml of acetic acid was refluxed overnight in 60 ml of ethanol. The mixture was cooled to room temperature and the solvent removed in vacuo. The residue was dissolved in 500 ml of ether and the solution was washed with 5% aqueous potassium carbonate (3×100 ml) and water (3×50 ml) and dried over sodium sulfate. Removal of the solvent gave the imine (5.2 g) as a light yellow solid which was used directly in the next step.

The imine (5.0 g, 17 mmol) was then dissolved in 75 ml of glyme and 4.1 ml (4.3 g, 21 mmol) of diisopropyl azodicarboxylate was added. The mixture was refluxed for 30 minutes and then the precipitate was collected by filtration and recrystallized from 700 ml of ethanol to give 2.7 g of the substituted xanthine as a white cotton-like solid, mp 284–286° C. $^1$H NMR (DMSO-d$_6$) δ0.92 (t, J=7 Hz, 2 H), 1.77 (sextet, J=7 Hz, 2 H), 3.28 (s, 3 H), 4.05 (t, J=7 Hz, 2 H), 7.50 (m, 3H), 8.15 (m, 2 H). IR (KBr) 3160, 1692, 1656 cm$^{-1}$. Anal. Calcd. for C$_{15}$H$_{16}$N$_4$O$_2$: C, 63.37; H, 5.67; N, 19.71 Found: C, 63.06; H, 5.78; N, 19.76. TLC: silica gel; ether:hexane, 55:45; blue fluorescense by UV; Rf=0.28.

EXAMPLE 3

Reversal of Histamine-Induced Broncoconstriction

Adult male guinea pigs, weighing 400–600 kg, were anesthetized with an intraperitoneal injection of urethane (1.5 gm/kg). After a midline neck incision, the carotid artery and jugular vein were cannulated using polyethylene tubing. The trachea was cannulated using a 15 gauge Leuer Stub. Animals were ventilated at a constant rate and volume (55 breaths per minute and 1 ml per 100 mg body weight) using a Harvard Apparatus small animal respirator. Airway pressure was measured from a side port of the tracheal cannula, using a Statham pressure transducer. Airway pressure and blood pressure were recorded using a Gould physiograph. Body temperature was maintained with a Narco temperature control unit.

Baseline airway and blood pressures were recorded for ten minutes. Aerosolized histamine (0.01%) was then delivered to the airways via a DeVilbiss ® ultrasonic nebulizer, inserted in-line between the respirator and the animal. After the histamine-induced bronchoconstriction reached a plateau, as evidenced by an increased airway pressure, a dose-response curve was determined for each compound. Drugs were delivered intravenously in increasing bolus doses, after the response to each preceding dose had peaked. The maximum effect of each compound was determined from the reversal of bronchoconstriction, as the percent decrease in the bronchoconstrictor response, after administration of the highest dose of that compound.

The $ED_{50}$ values and maximum effect (%) were calculated using SAS and PROBIT computer analysis. $ED_{50}$ is the dose of the test compound required to reverse the histamine response by 50%. The maximum effect is the maximum percent reversal of histamine-induced bronchoconstriction produced by the test compound. The results are reported in the Table.

EXAMPLE 4

Prevention of antigen-induced bronchoconstriction
Male Hartley guinea pigs were given two intraperitoneal injections each containing 50 mcg ovalbumin in a 2:1 emulsion of Freund's complete adjuvant and sterile saline, for a total of 100 mcg ovalbumin per animal. At least three weeks post sensitization injection, sensitized guinea pigs (now approximately 400-600 g) were anesthetized with an intraperitoneal injection of urethane. The carotid artery, jugular vein and the trachea were cannulated. The animal was ventilated as described in Example 3. Airway pressure was measured and aortic blood pressure was monitored. Body temperature was maintained.

Following a stabilization period of approximately ten minutes, drug in vehicle or vehicle alone was administered intravenously in a volume of 1 ml. All drugs were tested at a dose of 10 mg/kg. One minute post injection, ovalbumin (10 mg/ml) was aerosolized into the airway via a DeVilbiss ® ultrasonic nebulizer for a thirty minute period. Peak airway pressure attained during this thirty minute period was measured. The values, expressed as a percent of the increased airway pressure measured in those animals which received only vehicle, are given in the Table for the various test compounds.

EXAMPLE 5

Cardiovascular Effects

Male guinea pigs were anesthetized by urethane and the carotid artery and jugular vein were cannulated as described in Example 3. Aortic blood pressure was recorded from a pressure transducer and the signal was integrated to give a heart rate signal.

Each animal received a single intravenous injection of one compound. The dose of each compound was based upon the $ED_{50}$ value from the reversal of histamine-induced bronchoconstriction in the anesthetized guinea pig calculated in Example 3, thus the various compounds were studied at equipotent bronchodilator doses ($2 \times ED_{50}$). A group of control animals received injections of vehicle only. Changes in heart rate and blood pressure from pre-injection baseline values produced by drugs or vehicle were compared.

Acute toxicity of the xanthine derivatives was assessed in male CD-1 mice (20-30 g). Intraperitoneal injections of 125, 250 and 500 mg/kg doses of compound were give to 9 mice, 3 animals per dose. Treated animals were observed closely for side effects on the day of injection and once daily following the first 24 hours; daily observations continued for 14 days or until death. Results, expressed as a lethal dose range in a range of doses causing 0-100% fatality, are shown in the Table.

EXAMPLE 6

Emetic Effects

Male ferrets, 12-15 weeks old, were fasted overnight prior to experimentation. Animals were given intraperitoneal injections of 100 mg/kg of compound or were dosed with vehicle for controls. Animals were then placed in cages with feed and water and observed for signs of emesis. The number of animals exhibiting vomiting and/or wretching, as well as the number of episodes of emetic behavior, were noted during the first hour after injection. The results for various compounds tested are presented in the Table.

EXAMPLE 7

Adenosine Receptor Binding Assay

The potency of the 8-arylxanthine compounds to inhibit the specific binding of [$^3$H]cyclohexyladenosine ([$^3$H]CHA) to adenosine receptor sites on rat cortical membranes was examined using standard in vitro ligand binding techniques. The assay protocol utilized in these studies is a slight modification of the methods described by Bruns et al. (Proc. Natl. Acad. Sci. 77: 5547, 1980) and Williams et al. (Neurosci. Lett. 35:46, 1983). Briefly, rat cortical tissue was homogenized in ice cold 50 mM Tris HCl buffer (pH 7.4) using a Brinkman Polytron ®. The homogenate was centrifuged at $48,000 \times g$ for 10 minutes and the resulting tissue pellet was suspended in fresh cold buffer to yield a tissue concentration of 10 mg (wet weight)/ml. This tissue suspension was incubated for 30 minutes at 37° C. in the presence of adenosine deaminiase (0.2 I.U./mg tissue). Following this incubation, the tissue suspension was centrifuged as before and the resulting pellet was suspended in fresh buffer at a concentration of 7-10 mg tissue (wet weight)/ml. Inhibition of the specific binding of [$^3$H]CHA (New England Nuclear; 25 Ci/mmol) was examined in a total volume of 2 ml containing 50 mM Tris HCl, 7-10 mg of cortical tissue (1 ml of tissue suspension), 4 nM [$^3$H]CHA and various concentrations of the test compounds. Nonspecific binding was determined in the presence of $10^5$M 2-chloroadenosine. The binding reaction was carried out for 120 minutes at 23° C. and was terminated by vacuum filtration through Whatman GF/B filters using a Brandel M-48R Cell Harvester. The filters were washed 3 times with 3 ml of cold buffer and placed in scintillation vials in a Beckman LS 3801 scintillation counter. Dose-inhibition curves were generated with 10-12 concentrations of the test compound using triplicate incubations.

A similar procedure utilizing rat striatum homogenate and [$^3$H]NECA as ligand was employed to measure $A_2$-adenosine receptor binding.

The inhibition constants (Ki values) were calculated using EBDA, a log-logit iterative curve fitting program [McPhearson, Comput. Prog. Biomed., 107, 220 (1983)]. Results of this test are set forth in the Table.

TABLE

| Test system | 1-Methyl-3-propyl-8-phenylxanthine | 3-Methyl-1-propyl-8-phenylxanthine | 1,3-Dimethyl-8-phenylxanthine | 1,3-Dipropyl-8-phenylxanthine | Theophylline |
| --- | --- | --- | --- | --- | --- |
| Reversal of histamine- | 16.9 ± 2.0 (4) | 2.1 ± 0.4 (6) | >50 (4) | >50 (5) | 35.1 ± 5.3 (5) |

TABLE -continued

| Test system | 1-Methyl-3-propyl-8-phenylxanthine | 3-Methyl-1-propyl-8-phenylxanthine | 1,3-Dimethyl-8-phenylxanthine | 1,3-Dipropyl-8-phenylxanthine | Theophylline |
|---|---|---|---|---|---|
| induced bronchoconstriction, guinea pigs, $ED_{50}$, ± s.e.m. (N) mg/kg, i.v. maximum effect, % (N) ± s.e.m. | 56.3 ± 3.2 | 79.0 ± 3.4 | 22.0 ± 3.9 | 33.8 ± 8.5 | 72.8 ± 6.6 |
| Prevention of antigen-induced bronchoconstriction, guinea pigs, % control at 10 mg/kg, i.v. | 106.5 ± 9.7 (4) | 36.5 ± 2.0 (4) | 71.7 ± 1.6 (4) | 98.1 ± 12.4 (4) | 77.3 ± 8.1 (5) |
| Cardiovascular effects, guinea pigs, 2 × histamine- reversal $ED_{50}$, mg/kg, i.v. % Basal heart rate (N) % Basal blood pressure (mm Hg) | 104 ± 4 (5) 86 ± 10 | 100 ± 3 (5) 134 ± 7 | 102 ± 9 (3) 94 ± 22 | insoluble at 2 × $ED_{50}$ | 132 ± 4 (5) 66 ± 8 |
| Emetic effects, ferrets (100 mg/kg), i.p. no. responding / no. tested in 1 hour (episodes/responder ± s.e.) | — | 2/8 2 | 0/4 0 | — | 7/8 10.7 ± 3.7 |
| Acute Toxicity, mice, Approximate lethal dose, mg./kg, p.o., i.p. (comments) | >250 (3) | >500 (3) 250–500 (6) (sedation 6/6) | <250 (3) (sedation 3/3) | >250 (3) | >500 (3) 250–500 (6) (seizures 6/6) |
| $A_1$ - Adenosine receptor binding, Ki, nM ± s.e.m. | 6.3 ± 0.17 | 6.96 ± 0.91 | 60 ± 6 | 2.75 ± 0.29 | 4903 ± 1360 |
| $A_2$ - Adenosine receptor binding, Ki, nM ± s.e.m. | 93 ± 10.2 | 553 ± 55.7 | 644 ± 144 | 116 ± 100 | 13072 ± 1851 |

What is claimed is:

1. A method of treating bronchoconstriction comprising administering to a patient an effective amount of a compound of the formula

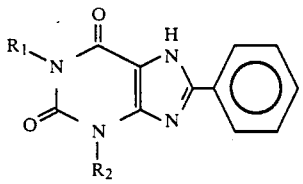

wherein
$R_1$ and $R_2$ are selected from saturated straight chain alkyls of one to eight carbons, with the proviso that $R_1$ and $R_2$ may not be the same,
or a pharmaceutically acceptable salt of such compound.

2. The method of claim 1 wherein in the compound which is administered $R_1$ and $R_2$ are straight chain alkyls of one to five carbons, with the proviso that either $R_1$ or $R_2$ must be an alkyl of at least three carbons.

3. The method of claim 1 wherein the compound in which $R_2$ is n-propyl and $R_1$ is methyl is administered.

4. The method of claim 1 wherein the compound in which $R_2$ is n-propyl and $R_1$ is methyl is administered.

* * * * *